United States Patent
Stephenson

(10) Patent No.: US 6,590,647 B2
(45) Date of Patent: Jul. 8, 2003

(54) PHYSICAL PROPERTY DETERMINATION USING SURFACE ENHANCED RAMAN EMISSIONS

(75) Inventor: Kenneth E. Stephenson, Newtown, CT (US)

(73) Assignee: Schlumberger Technology Corporation, Ridgefield, CT (US)

( * ) Notice: Subject to any disclaimer, the term of this patent is extended or adjusted under 35 U.S.C. 154(b) by 62 days.

(21) Appl. No.: 09/848,892

(22) Filed: May 4, 2001

(65) Prior Publication Data

US 2002/0163639 A1 Nov. 7, 2002

(51) Int. Cl.[7] .................................. G01J 3/44
(52) U.S. Cl. ..................... 356/301; 356/326; 356/307
(58) Field of Search ........................... 356/301, 326, 356/307

(56) References Cited

U.S. PATENT DOCUMENTS

| | | | |
|---|---|---|---|
| 3,770,350 A | * 11/1973 | Stone et al. ............... 356/301 |
| 3,780,575 A | 12/1973 | Urbanosky .................. 73/152 |
| 3,859,851 A | 1/1975 | Urbanosky .................. 73/155 |
| 4,994,671 A | 2/1991 | Safinya et al. ............. 250/255 |
| 5,166,747 A | 11/1992 | Schroeder et al. .......... 356/326 |
| 5,167,149 A | 12/1992 | Mullins et al. ............. 73/155 |
| 5,201,220 A | 4/1993 | Mullins et al. ............. 73/155 |
| 5,266,800 A | 11/1993 | Mullins ..................... 250/256 |
| 5,331,156 A | 7/1994 | Hines et al. ............... 250/256 |
| 5,751,415 A | * 5/1998 | Smith et al. ............... 356/301 |
| 5,822,058 A | * 10/1998 | Adler-Golden et al. ...... 356/303 |
| 5,841,545 A | * 11/1998 | Young ....................... 356/436 |
| 5,939,717 A | * 8/1999 | Mullins ..................... 250/255 |
| 6,023,340 A | 2/2000 | Wu et al. .................. 356/432 |
| 6,072,577 A | * 6/2000 | Wunderling et al. ........ 356/301 |
| 6,219,137 B1 | * 4/2001 | Vo-Dinh .................... 356/301 |
| 6,348,792 B1 | * 2/2002 | Beard et al. ............... 324/303 |
| 6,373,567 B1 | * 4/2002 | Wise et al. ................ 356/301 |
| 6,459,263 B2 | * 10/2002 | Hawkes et al. ............. 324/303 |

FOREIGN PATENT DOCUMENTS

JP      02000206048 A   *  7/2002

OTHER PUBLICATIONS

Applied Spectroscopy, vol. 34 (1980), pp. 411–414, Dwain E. Diller et al., "Composition of Mixtures of Natural Gas Components Determined by Raman Spectrometry".

(List continued on next page.)

Primary Examiner—Thien M. Le
Assistant Examiner—Allyson N Sanders
(74) Attorney, Agent, or Firm—William B. Batzer; John J. Ryberg

(57) ABSTRACT

A method of and apparatus for determining a physical property of a material. The method includes: attaching nanoparticles to a substrate; positioning the substrate near the material; illuminating the nanoparticles with photons having wavelengths that stimulate surface enhanced Raman emissions; detecting photons emitted as a result of the illumination; and determining said physical property of said material using said detected photons. The apparatus includes: a substrate; nanoparticles attached to the substrate; a light source, connected to the substrate, for illuminating the nanoparticles with photons having wavelengths that stimulate surface enhanced Raman emissions; a photodetector, connected to the substrate, for detecting photons emitted as a result of illumination of the nanoparticles; and a processor, connected to the photodetector, for determining a property of material near the nanoparticles from the detected photons. The inventive method and apparatus are particularly adapted for use in connection with hydrocarbon exploration and production activities.

21 Claims, 3 Drawing Sheets

OTHER PUBLICATIONS

Fiber Optic Sensors, (1991), pp. 333–335, ed. Eric Udd.

http://www-ece.rice.edu/~halas/research.html, Apr. 19, 2001, pp. 1–2, Halas Nanoengineering Group Research.

Journal Chem. Phys., vol. 111, (1999), pp. 4729–4735, S. J. Oldenburg, et al., "Surface Enhanced Raman Scattering in the Near Infrared Using Metal Nanoshell Substrates".

Journal Opt. Soc. Am., B/vol. 16, No. 10 (1999), pp. 1824–1832, Richard D. Averitt, et al., "Linear Optical Properties of Gold Nanoshells".

Surface Enhanced Raman Scattering, (1982), pp. 109–128, M. Kerker, et al., "Enhanced Raman Scattering by Molecules Adsorbed at the Surface Coloidal Particles".

Topics in Current Physics #11,(1979), "Raman Spectroscopy of Gases and Liquids" ed. A. Weber.

* cited by examiner

PHYSICAL PROPERTY DETERMINATION USING SURFACE ENHANCED RAMAN EMISSIONS

BACKGROUND OF THE INVENTION

The present invention relates to a method of and apparatus for determining a physical property of a material and is particularly related to a method of and apparatus for determining a physical property of a material using surface enhanced Raman emissions.

Various methods of and apparatus for determining physical properties of materials are commonly used in connection with hydrocarbon exploration and production activities. Optical fibers, for instance, require no electrical power and are inherently capable of operating at high temperature. Raman scattering within a fiber can be used to measure temperature as a function of position along the fiber and this is the basis of "distributed temperature sensor" systems. These types of systems are described in *Fiber Optic Sensors*, ed. Eric Udd, John Wiley & Sons NY(1991), incorporated herein by reference. Other types of fiber optic sensors can be constructed by adding mirrors or diffraction gratings to the fiber. But, even with these additions, there are many types of conventional sensors for which no fiber optic equivalent exists.

Another technology for producing sensors is "micromachining", and devices produced by this process which involve both mechanical and electrical components are called MEMS (Micro-Electro-Mechanical-Systems). These devices typically have dimensions on the order of $10^{-3}$ m and smallest features on the order of $10^{-6}$ m. Typically, these devices require electrical power to operate although some sensors have been produced which are energized optically. Devices that combine optics and micromachining are sometimes called MOEMS (Micro-Opto-Electro-Mechanical-Systems).

For borehole applications, it is often disadvantageous for sensors to require an electrical power source to operate. MOEMS devices may require electrical power to operate in addition to the light provided by the optical fiber. Each such device in the borehole must have a power supply means. If several MOEMS devices are distributed along an optical fiber, separate optical connections are required at each device. Connections are well known to be sources of failure in borehole equipment and having many such connections can make a system unreliable. Finally, each MOEMS device will likely require separate packaging, with ports to allow optical fiber entry and possibly ports to allow fluid entry. Having separate MOEMS packages distributed along the optical fiber will make installation along the well completion time consuming and difficult.

It is an object of the present invention to provide an improved method of and apparatus for determining a physical property of a material, particularly for use in connection with hydrocarbon exploration and production activities.

SUMMARY OF THE INVENTION

The present invention relates generally to a method of and apparatus for determining a physical property of a material and more particularly to a method of and apparatus for determining a physical property of a material using surface enhanced Raman emissions. The method includes: attaching nanoparticles to a substrate; positioning the substrate near the material; illuminating the nanoparticles with photons having wavelengths that stimulate surface enhanced Raman emissions; detecting photons emitted as a result of the illumination; and determining the physical property of the material using the detected photons. The apparatus includes: a substrate; nanoparticles attached to the substrate; a light source, connected to the substrate, for illuminating the nanoparticles with photons having wavelengths that stimulate surface enhanced Raman emissions; a photodetector, connected to the substrate, for detecting photons emitted as a result of illumination of the nanoparticles; and a processor, connected to the photodetector, for determining a physical property of material near the nanoparticles from the detected photons. The inventive method and apparatus are particularly adapted for use in connection with hydrocarbon exploration and production activities. The invention and its benefits will be better understood with reference to the detailed description below and the accompanying drawings.

DETAILED DESCRIPTION OF THE INVENTION

Figure 1:
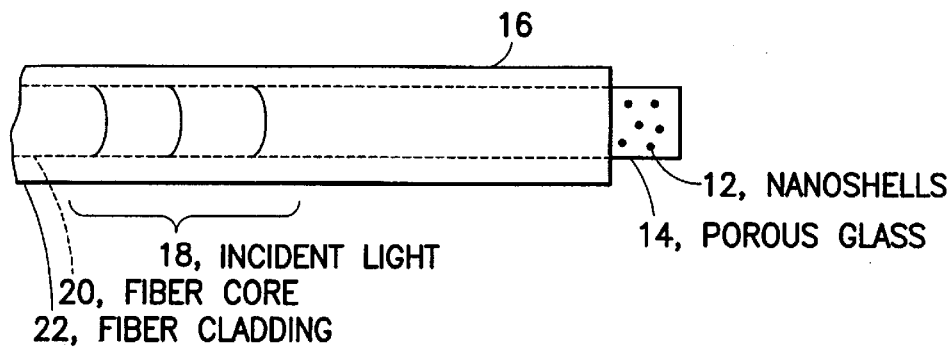
FIG. 1 illustrates nanoparticles attached to a porous glass probe.

The inventive method of and apparatus for determining a physical property of a material utilizes nanoparticles attached to a substrate. It is desirable to have sensors that are so small they can be embedded in a substrate, such as an optical fiber. It is also desirable to be able to extract power directly from the optical wave in the fiber and to communicate to the surface via the optical fiber. This is an attraction of nanotechnology. Nanotechnology is a term used to describe the fabrication, characteristics, and use of structures ("nanoparticles") with nanometer dimensions. Nanoparticles are so small that they exhibit quantum mechanical effects that allow them to interact strongly with light waves, even though the wavelength of the light may be much larger than the particle. Nanoparticles are frequently produced by chemical reactions in solutions. They are quite different from micro-machined (MEMS) devices, which do not exhibit quantum effects and are typically produced by lithographic techniques.

One type of nanoparticle is called a gold nanoshell. These types of particles are described in more detail in *Linear optical properties of gold nanoshells*, R. D. Averitt, et. al., J. Opt. Soc. Am B16 (1999) 1824 and *Surface enhanced Raman scattering in the near infrared using metal nanoshell substrates*, S. J. Oldenburg, et. al., J. Chem. Phys.111 (1999) 4729, both of which are incorporated herein by reference. Nanoshells are thin (approximately 2 nm thick) shells of noble metals (for example, gold, silver, or copper) covering a dielectric sphere (for example, silica or gold sulfide). All objects with a metal surface, including nanoshells, exhibit a phenomenon called "surface plasmon resonance" in which incident light is converted strongly into electron currents at the metal surface. The oscillating currents produce strong electric fields in the (non-conducting) ambient medium near the surface of the metal. The electric fields, in turn, induce electric polarization in the ambient medium. Electric polarization is well known to cause the emission of light at wavelengths characteristic of the medium, the Raman wavelengths. Additional background information regarding this phenomenon may be found in *Surface Enhanced Raman Scattering*, ed. Chang & Furtak, Plenum Press, NY(1982), incorporated herein by reference. Other types of nanoparticles are known that are capable of stimulating surface enhanced Raman emissions from nearby materials, such as gold clusters. In this application, the term Raman scattering is intended to encompass all related physical phenomena where the optical wave interacts with the polarizability of the material, such as Brillouin scattering or polariton scattering.

Detection and identification of the wavelengths of Raman emission can be used to "fingerprint" and identify the components of the ambient medium. The process of stimulating the surface plasmon resonance with light and subsequent emission of light at Raman wavelengths is called "surface enhanced Raman scattering" (SERS). The advantage of nanoshells for SERS is the ability to tune the wavelength of the surface plasmon resonance to any desired value by adjusting the thickness of the shell and diameter of the dielectric sphere. For purposes of this invention, it may be desirable to tune the resonance to the near infrared, where transmission through optical fiber glass is possible over long distances with little absorption and where inexpensive laser sources exist. Nanoshells may be obtained from The Halas Nanoengineering Group at Rice University, 6100 Main Street, Houston, Tex. 77005.

SERS has been shown to enhance the intensity of Raman scattering in material near the surface of the shell by as much as $10^6$. In *Surface enhanced Raman scattering in the near infrared using metal nanoshell substrates*, S. J. Oldenburg, et. al., J. Chem. Phys. 111 (1999) 4729, for instance, nanoshells were suspended in a colloidal solution containing the organic compound p-mercaptoaniline and the Raman scattering intensity was compared to the same solution without suspended nanoshells. The p-mercaptoaniline Raman enhancement in this case was reported to be a factor of approximately 200,000.

Raman scattering is commonly used in the laboratory as a sensitive fingerprint of molecular concentration. Raman spectra of natural gas mixtures and of $H_2S$ are known, for example, from publicly available scientific literature. See, for example, *Raman Spectroscopy of Gases and Liquids*, ed. A. Weber, Springer-Verlag Berlin (1979); and *Composition of Mixtures of Natural Gas Components Determined by Raman Spectrometry*, D. E. Diller, et. al., Appl. Spec. 34 (1980) 411, both of which are incorporated herein by reference. However, without an enhancement mechanism such as nanoshells, the low Raman intensity makes these measurements difficult to implement in a borehole, even though they are of interest for real-time monitoring of reservoir fluids. One of the benefits of the present invention is the ability to make such measurements viable in real-time in a borehole environment.

In an embodiment of this invention, shown schematically in FIG. 1, nanoparticles are attached to a substrate by embedding gold nanoshells 12 in a porous glass matrix 14 at the end of an optical fiber 16. Methods to produce porous glass are well known. For optimum performance, the index of refraction of the glass is preferably chosen to be higher than the surrounding material, which could be, for instance, reservoir fluids in a borehole. In FIG. 1, incident light 18, from a light source (discussed below) travels through the fiber core 20, reflecting internally as necessary at the interface between the fiber core and the fiber cladding 22, to the porous glass matrix 14. A portion of the incident light 18 passes through the porous glass matrix 14 and is absorbed by the nanoshells 12. A portion of the material in which the substrate is positioned, in this example natural gas, has adsorbed onto the nanoshells 12 and the photons in the incident light 18 stimulates surface enhanced Raman emissions from this material. A portion of these emissions return through the optical fiber 16 to a photodetector and processor which will be discussed in more detail below. Because the Raman signal from the fluids surrounding the nanoshells is enhanced, this type of sensor could be used in the borehole to sense $H_2S$ in gases and identify components of natural gases. It could also be used to identify components in borehole liquids.

Figure 2:
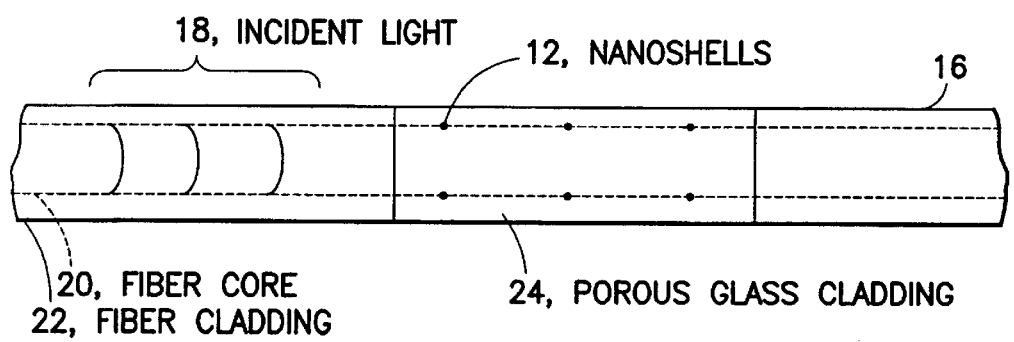
FIG. 2 illustrates nanoparticles attached to a fiber optic cable using porous glass cladding.

While the embodiment shown in FIG. 1 is simple and relatively easy to construct, it does not produce a distributed measurement. Shown in FIG. 2 is an embodiment of the inventive method and apparatus that may be used for this purpose. In this embodiment, short sections of fiber cladding 22 from the optical fiber 16 are replaced with porous glass cladding 24 having embedded nanoshells 12. The refractive index of the porous glass cladding 24 is chosen to be intermediate between the refractive index of the fiber cladding 22 and the fiber core 20. This ensures that some of the Raman light emitted by the material near the nanoshells 12 will be trapped and propagated along the core/cladding waveguide. As the Raman light emitted from one porous glass region travels through the core/cladding and reaches another porous glass region, some of the Raman light may escape through the porous glass section. In order to avoid excessive loss of Raman light, the total length of porous glass cladding 24 along the optical fiber 16 will typically be much less than the length covered by conventional fiber cladding 22.

Figure 3:
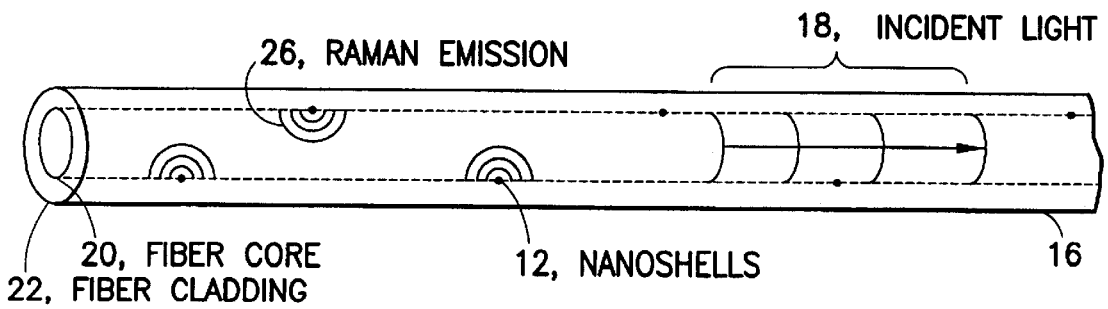
FIG. 3 illustrates nanoparticles embedded within a fiber optic cable near the core/cladding interface.

As discussed above, distributed temperature sensing in optical fibers by means of Raman backscattering is well known in the art. This method uses the fact that the ratio of Stokes to anti-Stokes Raman scattering in the silica of the fiber core is sensitive to temperature. Optical time domain reflectometry (OTDR) is used to obtain the temperature as a function of distance (travel time) along the fiber. One of the primary difficulties with this measurement is the low intensity of the Raman signal, due to low quantum mechanical cross-section for Raman scattering. This creates a low signal-to-noise (S/N) which limits the spatial resolution and temperature precision. The present invention may be used to increase the signal to noise ratio of the measurement to give better resolution and precision. A schematic diagram of this embodiment is shown in FIG. 3.

In this embodiment, gold nanoshells 12 may be embedded directly into the fiber core 20 of the optical fiber 16 itself or, alternatively, at the interface between the fiber core 20 and the fiber cladding 22. In FIG. 3, the nanoshells 12 are placed at the interface between the fiber core 20 and the fiber cladding 22. The nanoshells 12 are tuned (by choosing the appropriate shell thickness and diameter) to have surface plasmon resonance close to the wavelength of the incident light 18. The particular choice of wavelength is a compromise between maximizing the Raman emission 26 and moderating the attenuation of the incident light wave 18 due to interactions with the nanoshell 12. In other words, the resonance is chosen to optimize the production of Raman light per unit of absorption of incident light by the nanoshells 12. This embodiment demonstrates that it is not necessary for the nanoparticles to be immediately adjacent to the material being sensed. If the section of the optical fiber 16 shown in FIG. 3 is placed within borehole fluids, a physical property (temperature) of a nearby material (the fluids) may be determined from the stimulated surface enhanced Raman emissions even though the nanoparticles are not in physical contact with the borehole fluids.

Other methods for attaching the nanoparticles to the substrate are possible, such as by using reflectance matching adhesive or by creating micromachined receptacles for the nanoparticles.

Figure 4:
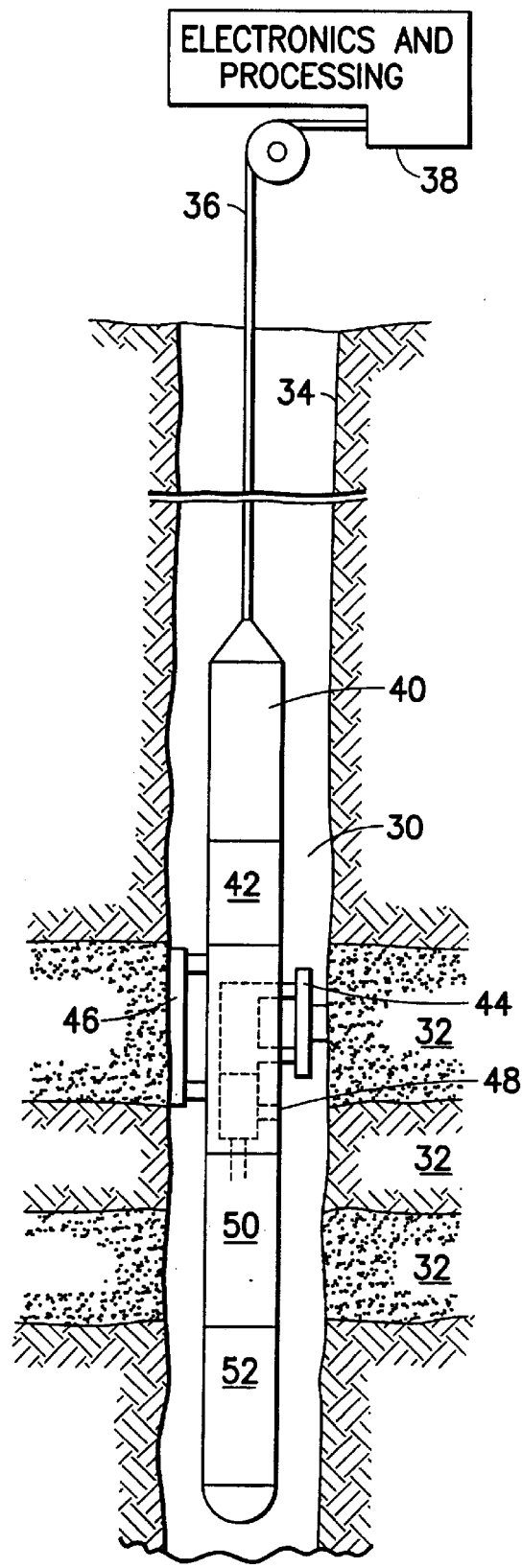
FIG. 4 illustrates the use of the inventive method and apparatus in a well logging application.

The present method and apparatus may be used, for instance, in a well logging environment, as shown in FIG. 4. Various methods for optically analyzing fluids using well logging equipment are known, such as those methods and apparatus described in commonly-owned U.S. Pat. Nos. 3,780,575; 3,859,851; 4,994,671; 5,167,149; 5,166,747; 5,201,220; 5,266,800; 5,331,156; 5,859,430; 5,939,717; and 6,023,340; each of which is incorporated herein by reference. In the embodiment shown in FIG. 4, for instance, a borehole logging tool 30 is shown for testing earth formations and analyzing the composition of fluids from the formation 32. The tool 30 is suspended in the borehole 34 from the lower end of a typical multi-conductor cable 36 that is spooled in the usual fashion on a suitable winch (not shown) on the surface. On the surface, the cable 36 is electrically connected to an electrical control system 38. The tool 30 includes an elongated body 40 which encloses the downhole portion of the tool control system 42. The elongated body 40 also carries a selectively extendible fluid admitting assembly 44 and a selectively extendible tool anchoring member 46 which are respectively arranged on opposite sides of the body. The fluid admitting assembly 44 is equipped for selectively sealing off or isolating selected portions of the wall of the borehole 34 such that pressure or fluid communication with the adjacent earth formation is established. Also included with tool 30 is a fluid analysis module 48 through which the obtained fluid flows. The fluid may thereafter be expelled through a port (not shown) or it may be sent to one or more fluid collecting chambers 50 and 52 which may receive and retain the fluids obtained from the formation. Control of the fluid admitting assembly 44, the fluid analysis module 48, and the flow path to the collecting chambers is maintained by the electrical control systems 38 and 42. The fluid analysis module 48 may contain, for instance, a porous glass probe having attached nanoparticles as shown in FIG. 1. By tuning the resonance of the nanoparticles to the wavelength of the light source or by adjusting the wavelength of the light source to match the resonant frequency of the nanoparticles, surface enhanced Raman emissions may be stimulated in the fluid and one or more physical properties of the fluid may be determined.

Figure 5:
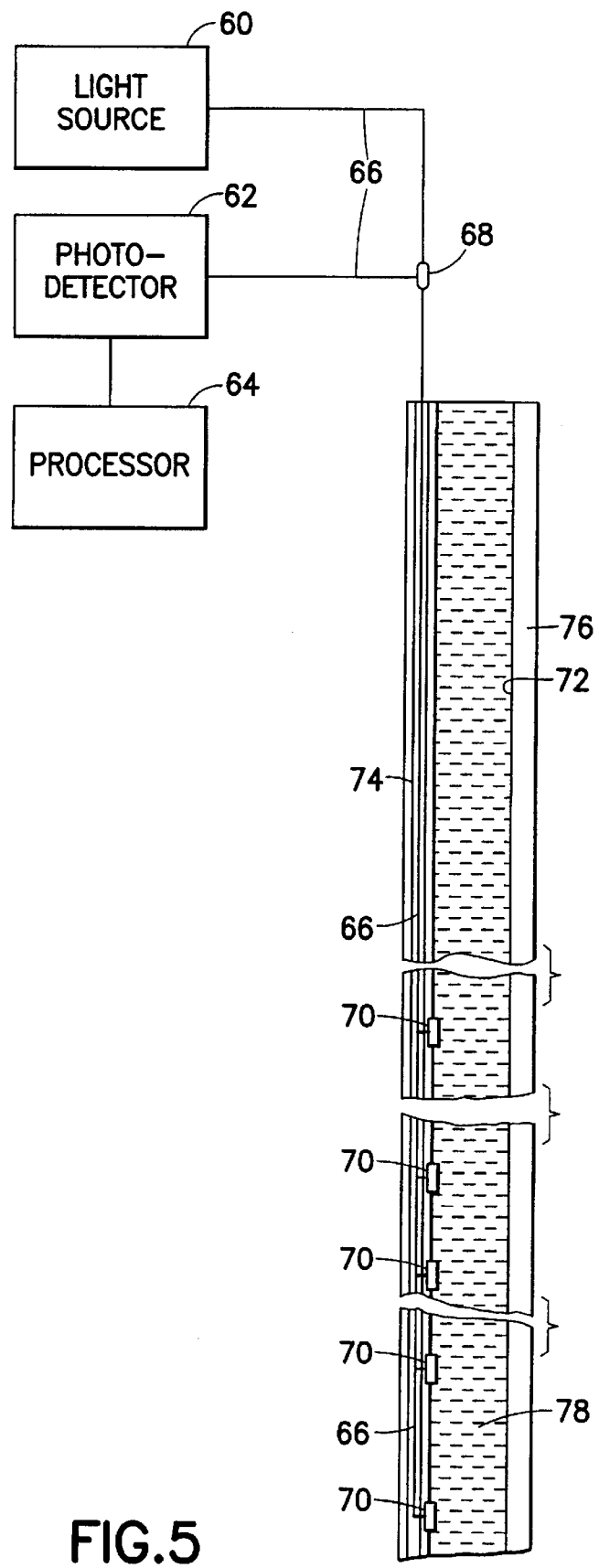
FIG. 5 illustrates the use of the inventive method and apparatus in a hydrocarbon reservoir monitoring application.

The present method and apparatus may also be used in a permanent hydrocarbon reservoir monitoring environment, as shown in FIG. 5. In FIG. 5, an uphole light source 60 is shown, which may produce a high amplitude near infrared signal at selected wavelengths (such as an Argon ion laser). Also shown in FIG. 5 are an uphole photodetector 62 (such as a spectrometer) and a processor 64 for processing signals received from the photodetector. Optical fibers 66 and a directional coupler 68 are used to connect the uphole light source 60 and the uphole photodetector 62 to a plurality of sensor sections 70 located at various locations of the wellbore 72. The optical fibers 66 are preferably run through a small diameter conduit 74 that is cemented in the annulus 76 surrounding the wellbore 72. Alternatively, the conduit 74 may be run inside the wellbore or production tubing. The sensor sections 70 may consist of the components illustrated schematically in FIGS. 1, 2, or 3. When a physical property of the borehole fluid 78 is intended to be determined, the nanoparticles within the sensor sections 70 must be sufficiently near the borehole fluid to allow the desired physical property to be determined from the stimulated surface enhanced Raman emissions. Components disclosed in commonly-assigned co-pending U.S. patent application Ser. No. 09/604,440, entitled "Permanent Optical Sensor Downhole Fluid Analysis Systems" and filed Jun. 26, 2000, incorporated herein by reference, may be used in the inventive method and apparatus. The components of the relatively simple sensor section 70 are particularly well adapted for the high temperature/high pressure conditions typically found in hydrocarbon exploration and production environments.

The foregoing descriptions of preferred and alternate embodiments of the present invention have been presented for purposes of illustration and description. They are not intended to be exhaustive or to limit the invention to the precise examples described. Many modifications and variations will be apparent to those skilled in the art. These embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the accompanying claims and their equivalents.

What is claimed is:

1. A method of determining a physical property of a material, said method comprising the steps of:

attaching nanoparticles to a substrate;

positioning said substrate near said material;

illuminating said nanoparticles with photons having wavelengths that stimulate surface enhanced Raman emissions;

detecting photons emitted as a result of said illumination; and determining said physical property of said material using said detected photons.

2. A method according to claim 1, wherein said substrate comprises an optical fiber.

3. A method according to claim 2, wherein said optical fiber consists of a fiber core surrounded by a fiber cladding, defining an interface therebetween, and said particles are located near said interface.

4. A method according to claim 1, wherein said substrate comprises porous glass.

5. A method according to claim 1, wherein said material is a fluid.

6. A method according to claim 1, wherein said material is located within a wellbore within the earth's subsurface.

7. A method according to claim 1, wherein said physical property is temperature.

8. A method according to claim 1, wherein said determining a physical property of said material comprises determining one or more chemical components of said material.

9. A method according to claim 1, wherein said material includes at least one of crude oil, natural gas, or water.

10. A method according to claim 1, wherein said substrate is located within a well logging tool.

11. A method according to claim 1, wherein said substrate is located beneath the surface of the earth, said nanoparticles are illuminated by a light source located above the surface of the earth, and said emitted photons are detected by a photodetector located above the surface of the earth.

12. An apparatus for determining a physical property of a material comprising:

a substrate;

nanoparticles attached to said substrate;

a light source, connected to said substrate, for illuminating said nanoparticles with photons having wavelengths that stimulate surface enhanced Raman emissions;

a photodetector, connected to said substrate, for detecting photons emitted as a result of illumination of said nanoparticles; and a processor, connected to said photodetector, for determining a physical property of material near said nanoparticles from photons detected by said photodetector.

13. An apparatus according to claim 12, wherein said substrate comprises an optical fiber.

14. An apparatus according to claim 13, wherein said optical fiber consists of a fiber core surrounded by a fiber cladding, defining an interface therebetween, and said particles are located near said interface.

15. An apparatus according to claim 12, wherein said substrate comprises porous glass.

16. An apparatus according to claim 12, wherein said physical property is temperature.

17. An apparatus according to claim 12, wherein said determining a physical property of said material comprises determining one or more chemical components of said material.

18. An apparatus according to claim 12, wherein said substrate is attached to a well logging tool.

19. An apparatus according to claim 12, wherein said substrate is located beneath the surface of the earth, said light source is located above the surface of the earth, and said photodetector is located above the surface of the earth.

20. An apparatus according to claim 19, wherein said photons produced by said light source have wavelengths in the near infrared spectrum.

21. An apparatus according to claim 12, wherein said substrate is located within a pipe carrying naturally occurring or processed hydrocarbons.

* * * * *